United States Patent [19]

Meconi et al.

[11] Patent Number: 5,885,612
[45] Date of Patent: Mar. 23, 1999

[54] RECRYSTALLIZATION-FREE ESTRADIOL-CONTAINING PATCH

[75] Inventors: Reinhold Meconi, Neuwied; Frank Seibertz, Bad Hönningen, both of Germany

[73] Assignee: LTS Lohmann Therapie-Systeme GmbH, Neuwied, Germany

[21] Appl. No.: 860,595

[22] PCT Filed: Dec. 18, 1995

[86] PCT No.: PCT/EP95/05005

§ 371 Date: Jul. 8, 1997

§ 102(e) Date: Jul. 8, 1997

[87] PCT Pub. No.: WO96/21433

PCT Pub. Date: Jul. 18, 1996

[30] Foreign Application Priority Data

Jan. 12, 1995 [DE] Germany ............. 195 00 662.3

[51] Int. Cl.⁶ .................................................. A61F 13/02
[52] U.S. Cl. ........................................... 424/448; 424/449
[58] Field of Search ............................ 424/448, 449

[56] References Cited

U.S. PATENT DOCUMENTS 4,624,665  11/1986  Nuwayser ....................... 604/307
5,393,529   2/1995  Hoffmann ....................... 424/445
5,503,844   4/1996  Kwiatek ......................... 424/449
5,518,734   5/1996  Stefano .......................... 424/448

FOREIGN PATENT DOCUMENTS

| 0 072 251 | 2/1983  | European Pat. Off. |
| 0 186 019 | 7/1986  | European Pat. Off. |
| 0 275 716 | 7/1988  | European Pat. Off. |
| 0 285 563 | 10/1988 | European Pat. Off. |
| 0 328 806 | 8/1989  | European Pat. Off. |
| 2 006 969 | 10/1970 | Germany . |
| 3 843 239 | 2/1990  | Germany . |
| 3 205 258 | 2/1991  | Germany . |
| 3 743 946 | 6/1991  | Germany . |
| 3 933 460 | 3/1992  | Germany . |
| 87/07138  | 12/1987 | WIPO . |

*Primary Examiner*—D. Gabrielle Brouillette
*Attorney, Agent, or Firm*—Wenderoth, Lind & Ponack, L.L.P.

[57] ABSTRACT

An active substance-containing patch for the controlled release of estradiol or its pharmaceutically acceptable derivatives alone or combined with gestagens, comprising a backing layer, an active substance-containing reservoir which is bonded thereto and produced by using pressure-sensitive adhesives, and a removable protective layer, is characterized by the fact that the pressure-sensitive adhesive comprises ethylcellulose, esters of non-hydrogenated and/or hydrogenated colophony, and lauric acid.

18 Claims, No Drawings

RECRYSTALLIZATION-FREE ESTRADIOL-CONTAINING PATCH

This application is a 371 of PCT/EP95/05005, filed Dec. 18, 1995.

BACKGROUND OF THE INVENTION

The present invention relates to an active substance-containing patch for the controlled release of estradiol or its pharmaceutically acceptable derivatives either alone or combined with gestagens, to human or animal skin, comprising a pressure-sensitive adhesive of ethylcellulose, esters of colophony, and lauric acid. The present invention further relates to its use and to a process for its production.

Estrogen-containing patches have been known for some time. However, these patches are disadvantageous in that they either contain ethanol or involve the potential danger of active substance recrystallization in the course of time.

It is known from DE-OS 32 05 258 and EP 0 285 563 to administer estradiol and ethanol simultaneously in a patch formulation. However, the production of this patch is very expensive, and there is a low wearing comfort after application because of inflexibility.

EP 0 285 563 describes a transdermal therapeutic system for the combined application of estrogens and gestagens. The reservoir comprises the active substance formulation, and optionally a membrane, as well as ethanol as a percutaneous absorption improving agent. Since the active substance release is primarily controlled by the membrane, this transdermal therapeutic system is completely different from the active substance-containing patch according to the present invention. In the patch described in said publication, the adhesive has the mere function of fastening the patch to the skin. The fact that it can contribute to the control of the active substance release is not its main function but merely a—probably even undesired—side effect. It is a so-called "pouch patch" since the active substance preparation is present in a pouch consisting of an impermeable backing layer and a membrane having an adhesive layer. Owing to its complicated structure production of this patch is very expensive since the individual components have to be manufactured separately and then joined in an additional step to form a patch.

Unlike the single-layer system according to the present invention EP 0 275 716 describes a two-layer transdermal system for the simultaneous administration of one or several estrogens which are dissolved or microdispersed in the polymeric layer. In addition to the active substances, the pressure-sensitive adhesive layer comprises substances improving the transdermal absorption. Polymeric and pressure-sensitive adhesive layer may consist of polyacrylates, silicones, or polyisobutylenes.

EP 0 072 251 describes a flexible, liquid-absorbing medicinal bandage. The substrate attached to the flexible backing layer consists of a hydrophilic matrix based on hydrophilic high-molecular polysaccharides and/or polyacrylic acid, polyacrylamide, ethylene-vinyl acetate-copolymers, and other polymers, as well as of a liquid phase based on a solution or emulsion of carbohydrate, proteins, polyhydric alcohols, and different active substances, amongst others hormones. The main feature of this invention is the moisture-absorbing adhesive.

EP 0 328 806 describes a transdermal therapeutic system without membrane; its matrix consists of a polyacrylate adhesive, a solvent, a penetration enhancer, and estrogen, its derivatives and combinations thereof.

WO 87/07 138 describes an estradiol patch having a backing layer, an active substance-containing matrix, and a pressure-sensitive adhesive covered with a removable protective layer. Matrix and pressure-sensitive adhesive are manufactured in operations involving considerable technological expenditure, i.e., by homogenizing, degassing, coating, drying, and separating. According to an embodiment the backing layer has to be coated with a pressure-sensitive adhesive, requiring an additional operation. The individual parts are joined in a separate step. For this reason, the production of this patch is very expensive and complicated.

U.S. Pat. No. 4,624,665 describes systems comprising the active substance in microencapsulated form within the reservoir. The reservoir is embedded between backing layer and a membrane. The outer edge of the system is provided with a pressure-sensitive adhesive. Structure and production of this system are very complicated since the active substance has to be microencapsulated and homogeneously dispersed in a liquid phase which is then embedded between backing layer and membrane in further operations. Moreover, this system must then be provided with an adhesive edge and covered with a protective layer.

EP 0 186 019 describes active substance patches wherein water-swellable polymers are added to a rubber/adhesive-resin-mass and from which estradiol can be released. It turned out, however, that the estradiol release from these active substance patches is absolutely insufficient and fails to meet the therapeutic requirements.

DE-OS 20 06 969 describes a patch or a pressure-sensitive adhesive dressing exhibiting system action, wherein contraceptive substances are incorporated in the adhesive component or in the adhesive film. The adhesive film may be an acrylate.

DE-OS 39 33 460 describes an estrogen-containing active substance patch based on homo and/or copolymers with at least one derivative of acrylic acid or with methacrylic acid combined with water-swellable substances.

However, it turned out that the active substance release of pressure-sensitive adhesive transdermal therapeutic matrix systems which comprise the active substance in a partially or completely dissolved form is absolutely insufficient; moreover, they involve the potential risk that the active substance recrystallizes in the course of time. As a result the active substance release decreases, and the estrogen-containing patch does no longer meet the therapeutic requirements.

SUMMARY OF THE INVENTION

Accordingly, it is the object of the present invention to avoid the aforementioned drawbacks and to provide a stable, i.e., recrystallization-free, estrogen-containing patch having a sufficient active substance release which does not change through storage.

Most surprisingly, it turned out that this object is achieved by an estrogen-containing pressure-sensitive adhesive of ethylcellulose, esters of colophony, and lauric acid.

Accordingly, the above object is achieved by an active substance-containing patch according to the main claim. The subclaims relate to particularly preferred embodiments of the subject matter according to the present invention.

DETAILED DESCRIPTION OF THE INVENTION

Thus the present invention relates to an active substance-containing patch for the controlled release of estradiol or its pharmaceutically acceptable derivatives alone or combined with gestagens, consisting of a backing layer, an active substance-containing reservoir which is bonded thereto and is produced by using pressure-sensitive adhesives, and a removable protective layer, the pressure-sensitive adhesive comprising ethylcellulose, esters of non-hydrogenated and/ or hydrogenated colophony, and lauric acid.

Ethylcellulose is a cellulose ether produced by reacting ethyl chloride with alkali cellulose. With respect to the structure, it is generally assumed that a cellulose molecule is a chain of anhydroglucose or cellobiose units bound by oxygen bridges. These long chains of anhydroglucose with oxygen bridges are very stable and have good flexibility. These properties are utilized in the estradiol-containing patch according to the present invention to render the pressure-sensitive adhesive sufficiently cohesive, this is required to remove the patch from the skin without leaving any residue after completed application. The pressure-sensitive adhesive comprises ethylcellulose in a proportion of 5–25% wt., preferably 8–14% wt.

Examples of esters of colophony include, for example, methyl ester, glycerol ester, pentaerythritol ester, pentaerythritol ester modified with maleic acid, glycerol ester modified with maleic acid, and triethylene glycol ester. The proportion of colophony esters in the estradiol-containing pressure-sensitive adhesive amounts to 50–90% wt., preferably 60–80% wt.

The pressure-sensitive adhesive may comprise esters of hydrogenated colophony either alone or together with esters of non-hydrogenated colophony.

Particularly preferred esters of colophony include triethylene glycol ester, glycerol ester, and pentaerythritol ester of hydrogenated colophony.

Lauric acid is a basic carboxylic acid having 12 C-atoms. It increases the penetration of estradiol through the skin. The mechanism is still open. The proportion of lauric acid contained in the pressure-sensitive adhesive amounts to 1–20% wt., preferably 2–15 % wt.

The reservoir of the recrystallization-free, estradiol-containing patch with sufficient active substance release comprises estradiol and its pharmaceutically acceptable derivatives alone or in combination with gestagens at a total concentration of $1 \propto 15\%$ wt., relative to all of the reservoir components, namely in a molar ratio of 1:1 to 1:10.

The estradiol-containing reservoir may comprise at least one component of the group including anti-ageing agents, plasticizers, antioxidants, and absorption improvers. Suitable plasticizers are known to those skilled in the art and are described, for example, in DE 37 43 946. Usually, the proportion of plasticizers in the estradiol-containing reservoir amounts to up to 5%-wt.

In addition, the active substance-containing reservoir also comprises anti-ageing agents in a concentration of up to 1% wt. These are known to the skilled artisan and are described, for example, in DE 37 43 946.

The materials for the impermeable backing layer and the removable protective layer are also known to the skilled artisan (e.g., DE 38 43 239).

The estradiol-containing reservoir may either be produced from solution or from the melt.

Moreover, the reservoir may consist of several layers.

In case the reservoir has an insufficient self-tackiness to the skin, it may be provided with an additional pressure-sensitive adhesive layer which is free from active substances, or with a circumferential pressure-sensitive adhesive edge. This ensures that the transdermal patch adheres to the skin over the whole application period.

A particularly preferred structure of the transdermal estradiol-containing patch is a matrix system wherein, as is generally known, the matrix controls the active substance release and complies with the √t-law according to Higuchi. However, it is understood that a membrane system may well be of advantage in particular cases. In this case, a membrane controlling the active substance release is located between the reservoir and the pressure-sensitive adhesive layer.

The thickness of the transdermal patch depends on the therapeutic requirements and may be adapted accordingly. Usually, it ranges from 0.03–0.6 mm.

EXAMPLE 1

75.0 g triethylene glycol ester of hydrogenated colophony (Staybelite Ester 3E/by Hercules) and 10.0 g glycerol ester of hydrogenated colophony (Staybelite Ester 10E/by Hercules)

are mixed by kneading at 100° C. for 5 minutes. Then 2.5 g estradiol and 2.5 g lauric acid are added. Kneading is continued for 30 minutes. After heating to 140° C., 10.0 g ethylcellulose N50NF (by Hercules) are added in portions, and then kneading is continued for another 2.5 hours.

In a hotmelt coating line (die coating system) the active substance-containing adhesive mass thus obtained is coated onto a removable protective layer (Hostaphan RN 100, coated on one side with silicone—by Kalle) in such a manner that an active substance-containing reservoir having a mass per unit area of 80 g/m$^2$ results. The impermeable backing layer (polyester sheet, thickness 15 $\mu$m) is laminated on this reservoir. Subsequently, active substance patches of 16 cm$^2$ are punched.

EXAMPLES 2 AND 3

Manufacture is carried out as described in Example 1, however with the raw materials and quantities as listed in Table 1 (manufacturing formula).

Analytic procedure

The active substance release of the transdermal patches having a size of 16 cm$^2$ is determined according to the Rotating bottle-method described in USP XXII in 0.9% salt solution at 37° C.

To measure the guinea pig penetration, the skin of guinea pigs is clamped in the Franz-cell. An estradiol-containing patch having an area of 2.54 cm$^2$ is stuck onto the skin, and the active substance release is measured at 37° C. (acceptor medium: 0.9% salt solution). (Literature: Umesh V. Banakar Pharmaceutical dissolution testing (1st edition—1991)).

Testing as to recrystallization is carried out visually against the light.

The results are listed in Table 2.

TABLE 1

| | Composition (indications in g) | | | | |
|---|---|---|---|---|---|
| | Ethylcellulose | Staybelite Ester | | | |
| Example | N50NF | 3E | 10E | Lauric acid | Estradiol |
| 1 | 10.0 | 75.0 | 10.0 | 2.5 | 2.5 |
| 2 | 10.0 | 70.0 | 10.0 | 7.5 | 2.5 |
| 3 | 13.0 | 65.5 | 9.0 | 10.0 | 2.5 |

TABLE 2

Results of Analysis

| Example | Estradiol content μg/16 cm² | In-vitro release μg/16 cm² · 4 h | Guinea pig skin penetration μg/16 cm² · 24 h | Recrystallization |
|---|---|---|---|---|
| 1 | 3200 | 645 | 179 | no |
| 2 | 3200 | 843 | 157 | no |
| 3 | 3200 | 1368 | 180 | no |
| acc. to DE 3933460 | 3200 | 1125 | 95 | considerable |

The Table shows that a clearly improved penetration through the guinea pig skin is obtained, as evidenced by the Comparative Example according to DE 3933460. Analogously, there is no recrystallization at all in the Examples according to the present invention.

We claim:

1. A recrystallization-free estradiol-containing patch for the controlled release of estradiol or its pharmaceutically acceptable derivatives alone or in combination with at least one gestagen, comprising a backing layer, an active substance-containing reservoir, and a removable protective layer wherein said reservoir is bonded to said backing layer and contains a pressure-sensitive adhesive comprising 5–25%-wt. ethylcellulose, 50–90%-wt. of esters of non-hydrogenated and/or hydrogenated colophony, and 1–20%-wt. lauric acid.

2. The active substance-containing patch according to claim 1 wherein the pressure-sensitive adhesive comprises lauric acid in a proportion of 2–15%-wt.

3. The active substance-containing patch according to claim 1 wherein the pressure-sensitive adhesive comprises 8–14%-wt. of ethylcellulose.

4. The active substance-containing patch according to claim 1 wherein the pressure-sensitive adhesive comprises esters of colophony in a proportion of 60–80%-wt.

5. The active substance-containing patch according to claim 1 wherein the pressure-sensitive adhesive comprises estradiol or its pharmaceutically acceptable derivatives alone or in combination with at least one gestagen in a proportion of 1–15%-wt.

6. The active substance-containing patch according to claim 4 wherein the pressure-sensitive adhesive comprises estradiol or its pharmaceutically acceptable derivatives alone or in combination with at least one gestagen at a proportion of 1.5–5.0%-wt.

7. The active substance-containing patch according to claim 1 wherein the pressure sensitive adhesive comprises 2–15%-wt. lauric acid, 8–14%-wt. ethylcellulose and 60–80%-wt. colophony.

8. The active substance-containing patch according to claim 1 wherein the backing layer is impermeable to the components of the reservoir.

9. The active substance-containing patch according to claim 1 wherein the esters of colophony are selected from the group consisting of methyl ester, glycerol ester, pentaerythritol ester, pentaerythritol ester modified with maleic acid, glycerol ester modified with maleic acid, and triethylene glycol ester.

10. The active substance-containing patch according to claim 1 wherein the reservoir comprises estradiol or its pharmaceutically acceptable derivatives in combination with at least one gestagen in a molar ratio of 1:1 to 1:10.

11. The active substance-containing patch according to claim 1 wherein the reservoir comprises at least one component of the group consisting of anti-aging agents, plasticizers, antioxidants, and absorption improvers.

12. The active substance-containing patch according to claim 1 wherein the pressure-sensitive adhesive is a solvent-based pressure-sensitive adhesive or a hot-melt pressure-sensitive adhesive.

13. The active substance-containing patch according to claim 1 wherein the reservoir consists of several layers and has an additional pressure-sensitive adhesive layer which is free from active substances.

14. The active substance-containing patch according to claim 13 wherein a membrane which controls the active substance release and is located between the reservoir and the pressure-sensitive adhesive layer.

15. The active substance-containing patch according to claim 1 wherein the reservoir is provided with a circumferential pressure-sensitive adhesive edge.

16. The active substance-containing patch according to claim 1 wherein the thickness of the active substance-containing patch is in the range of 0.03–0.6 mm.

17. A recrystallization-free estradiol-containing patch for the controlled release of estradiol or its pharmaceutically acceptable derivatives alone or in combination with at least one gestagen, comprising a backing layer, an active substance-containing reservoir, and a removable protective layer, wherein said reservoir is bonded to said backing layer and contains a pressure-sensitive adhesive consisting essentially of 5–75% wt. ethylcellulose, 50–90% wt. esters of non-hydrogenated and/or hydrogenated colophony and 1–20% wt. lauric acid.

18. A method of using the active substance-containing patch according to claim 1 or 17 for therapeutic purposes in human and veterinary medicine or in cosmetics comprising removing the said removable protective layer from the patch and placing the patch on the skin of a human or animal.

* * * * *